US007067504B2

(12) United States Patent
King et al.

(10) Patent No.: US 7,067,504 B2
(45) Date of Patent: Jun. 27, 2006

(54) DI-STEROIDAL PRODRUGS OF ETHINYL ESTRADIOL

(75) Inventors: John Alexander King, Sallins (IE); James Keown, Kilkeel (IE); James William McIlroy, Belfast (IE); William Paul Armstrong, Belfast (IE); Michael Anthony McKervey, Belfast (IE); Austin McMordie, Craigavon (IE)

(73) Assignee: Warner Chilcott Company, Inc., Fajardo, PR (US)

( * ) Notice: Subject to any disclaimer, the term of this patent is extended or adjusted under 35 U.S.C. 154(b) by 0 days.

(21) Appl. No.: 11/009,617

(22) Filed: Dec. 10, 2004

(65) Prior Publication Data

US 2005/0159609 A1    Jul. 21, 2005

Related U.S. Application Data

(60) Provisional application No. 60/536,526, filed on Jan. 15, 2004.

(51) Int. Cl.
*A01N 31/56* (2006.01)
*C07J 9/00* (2006.01)
*C07C 49/00* (2006.01)
*C07C 49/423* (2006.01)

(52) U.S. Cl. ............... 514/182; 514/169; 514/170; 552/201; 552/203; 552/205; 552/502; 552/540; 552/541

(58) Field of Classification Search ............ 552/541, 552/540, 201, 203, 205; 514/169, 182, 177, 514/170
See application file for complete search history.

(56) References Cited

U.S. PATENT DOCUMENTS

| | | | | |
|---|---|---|---|---|
| 3,766,223 A | * | 10/1973 | Ercoli et al. | 552/509 |
| 3,828,081 A | | 8/1974 | Ercoli et al. | 260/397.2 |
| 3,916,002 A | | 10/1975 | Taubert et al. | 260/397.4 |
| 3,952,030 A | | 4/1976 | Chambers et al. | 260/397.4 |
| 4,002,747 A | | 1/1977 | van der Vies | 424/243 |
| 4,198,405 A | | 4/1980 | Enomoto et al. | 424/242 |
| 4,310,511 A | | 1/1982 | Holick | 424/59 |
| 5,117,015 A | | 5/1992 | Yarino et al. | 552/541 |
| 5,610,149 A | | 3/1997 | Burrows et al. | 514/169 |
| 5,760,214 A | * | 6/1998 | Zheng et al. | 540/109 |
| 5,888,996 A | | 3/1999 | Farb | 514/182 |
| 5,955,068 A | | 9/1999 | Gouin et al. | 424/78.17 |
| 5,989,581 A | | 11/1999 | Groenewegen | 424/433 |
| 6,028,207 A | * | 2/2000 | Zheng et al. | 552/203 |
| 6,083,941 A | | 7/2000 | Farb | 514/177 |
| 6,375,930 B1 | | 4/2002 | Young et al. | 424/9.362 |
| 6,441,206 B1 | | 8/2002 | Mikkonen et al. | 552/540 |
| 2002/0131991 A1 | | 9/2002 | Milstein et al. | 424/439 |

FOREIGN PATENT DOCUMENTS

| | | |
|---|---|---|
| DE | 1 123 666 | 10/1959 |
| DE | 2 330 581 | 1/1975 |
| FR | 2 297 629 | 1/1975 |
| JP | 35-004967 | 5/1960 |
| NL | 7 308 083 | 12/1974 |
| WO | WO 98/52965 | 11/1998 |

OTHER PUBLICATIONS

Hu Zheng et al., Abstract of "Studies on polymer-supported drugs: synthesis of poly(ethylene glycol)-estrogen compounds," Chemical Abstracts Service (XP002322263), and Yaoxue Xuebac(Database Accession No. 1988:423178), 1987, 637-40.
Huai-De Shu et al., Abstract of "Structure-activity relationships of estradiol derivatives," Chemical Abstracts Service (XP002322264), and Yaoxue Xuebao (Database Accession No. 1979:604845), 1979, 14(6), 343-8.
W. Dirscherl, "Uber Kohlensaurederivate des Follikelhormons. 7. Mitteilung uber Sexualhormone und verwandte Stoffe" Hoppe Seyler Zeitschrift Fur Physiol. Chemie, vol. 239, 1936, pp. 49-52. Translation included.
K. Parfitt, "Martindale—The Complete Drug Reference," 32ed, 1999, Pharmaceutical Press, pp. 1455-1458.
K. Fotherby, "Intrasubject Variability in the Pharmacokinetics of Ethynyloestradiol," Journal of Steroid Biochemistry and Molecular Biology, vol. 38, No. 6, 1991, pp. 733-736.
K. Fotherby, "Pharmacokinetics of Ethynyloestradiol in Humans," Methods and Findings in Experimental Clinical Pharmacology, 1982, 4(2), pp. 133-141.
E. Diczfalusy, O. Ferno, H. Fex, and B. Hogberg, "Long-Acting p-Alkoxyhydrocinnamic Acid Esters of Steroid Hormones," Acta Chemica Scandinavica, 1963, 17, pp. 2536-2547.
J. Fried and N.A. Abraham, "The Effect of Co-Solvents on Metal in Ammonia Reductions, The Formation of Dimeric Steroid Hormones," Tetrahedron Letters, 1964, No. 28, pp. 1879-1885.

(Continued)

*Primary Examiner*—Sabiha Qazi
(74) *Attorney, Agent, or Firm*—Fitzpatrick, Cella, Harper & Scinto

(57) ABSTRACT

The present invention is a di-steroidal prodrug of ethinyl estradiol according to formula I:

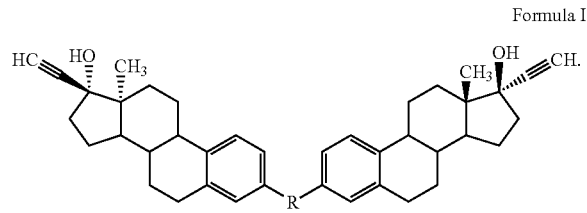

Formula I

14 Claims, No Drawings

OTHER PUBLICATIONS

H. Kuhl and H. Taubert, "A New Class of Long-Acting Hormonal Steroid Preparation: Synthesis of Oligomeric Estradiol Derivatives," Steroids, Jul. 1973, 22, pp. 73-87.

H. Kuhl and H. Taubert, "A New Class of Long-Acting Hormonal Steroid Preparation: Synthesis of Dimeric Ethynodiol and Nortestosterone, or Dimeric and Trimeric Androgens and of Some Dimeric Combinations of Steroids," Steroids, 1974, vol. 24, No. 5, pp. 613-626.

H. Kuhl, W. Auerhammer, and H. Taubert, "Oligomeric Oestradiol Esters: A New Class of Long-Acting Oestrogens," Acta Endrocrinologica, 1976, 83, pp. 439-448.

R. Vitali, S. Gladiali, G. Falconi, G. Celasco, M.A. Saccani, and R. Gardi, "Disteroidyl Ethers. 1. Synthesis and Oral Long-Lasting Uterotrophic Activity of 1,3,5(10)-Estratrien-17-γl Enol Ethers of 3-Keto Steroids,"Journal of Medicinal Chemistry, 1977, vol. 20, No. 3, pp. 359-364.

A. Ius, G. Meroni, and L. Ferrara, "Two Dimers, 4:4'-and 2:2'-Di[estradio], Obtained by Chemical Oxidative Coupling Coupling of Estradiol," Journal of Steroid Biochemistry, vol. 8, pp. 1259-1261.

D. Rabouin, V. Perron, B. N'Zemba, R. Gaudreault, and G. Berube, "A Facile Synthesis of $C_2$-Symmetric 17β-Estradiol Dimers," Bioorganic & Medicinal Chemistry Letters, 2003, 13, pp. 557-560.

* cited by examiner

DI-STEROIDAL PRODRUGS OF ETHINYL ESTRADIOL

CROSS REFERENCE TO RELATED APPLICATIONS

This application claims the benefit of U.S. Provisional Application Ser. No. 60/536,526 filed on Jan. 15, 2004.

BACKGROUND OF THE INVENTION

1. Field of the Invention

This invention is directed to a di-steroidal prodrug of ethinyl estradiol and pharmaceutically acceptable salts thereof. The invention also includes pharmaceutical dosage units of the di-steroidal prodrug and a method of forming the di-steroidal prodrug of ethinyl estradiol.

2. Related Background Art

Unbound 17β-estradiol is the most active, naturally occurring human estrogen. However, due to poor absorption and extensive first-pass metabolism in the gastrointestinal tract and liver following oral absorption, it is not generally orally active. Methods of increasing activity have included the use of micronized drugs to improve absorption and the use of prodrugs such as estradiol-17-valerate and equine estrogens which are a combination of sulphate and glucuronide derivatives (Martindale $32^{ed}$, 1999, Pharmaceutical Press).

Another method of increasing activity is to alter the structure of the 17β-estradiol. Ethinyl estradiol is an example of this. The ethinyl group on the 17 position greatly reduces liver first-pass metabolism compared to 17β-estradiol, enabling the compound to be more active than the natural estrogen, 17β-estradiol (Martindale $32^{ed}$, 1999, Pharmaceutical Press).

Ethinyl estradiol is the most common estrogen used in contraceptive preparations. Given its increased potency over 17β-estradiol it is used in comparatively lower doses (i.e., orally 15 to 50 μg per day) (Martindale $32^{ed}$, 1999, Pharmaceutical Press). It is also more potent by other routes of administration, i.e., vaginally where it can be employed at a daily dose of 15 μg (see U.S. Pat. No. 5,989,581). It has also been used in Hormone Replacement Therapy although to a lesser extent than 17β-estradiol.

U.S. Pat. No. 3,916,002 to Taubert et al. describes a number of oligomeric steroid esters having the formula: R—O—CO—(CH$_2$)$_n$—CO—O—R, wherein n is between 2 and 8, and each R is a monovalent steroid radical. The steroid radical is derived from steroids having a hydroxyl substituent at one of the carbon atoms numbered 3, 16 or 17. They can be produced by esterification of the two carboxyl radicals of a dicarboxylic acid with a steroid alcohol having a hydroxyl radical substituent at carbon atoms numbered 3, 16, or 17. However, Taubert et al. does not disclose a novel di-steroidal prodrug of ethinyl estradiol that is linked at the 3'C position of the ethinyl estradiol moiety.

While ethinyl estradiol has been preferred over 17β-estradiol for use in contraception, there are some disadvantages associated with the use of ethinyl estradiol. For example, not all of the ethinyl estradiol that is administered is biologically available. Ethinyl estradiol is metabolized in the intestinal wall and liver, which affects its bioavailability. Moreover, its bioavailability may vary somewhat from individual to individual (Journal of Steroid Biochemistry and Molecular Biology, 1991; 6: 733–736). In addition, it has been observed that as ethinyl estradiol is metabolized in the liver, enterohepatic recycling occurs (Methods And Findings in Experimental Clinical Pharmacology, 1982; 4: 133–42).

A novel prodrug of ethinyl estradiol, that impoves bioavailability would be highly advantageous.

SUMMARY OF THE INVENTION

The present invention is a di-steroidal prodrug of ethinyl estradiol according to formula I:

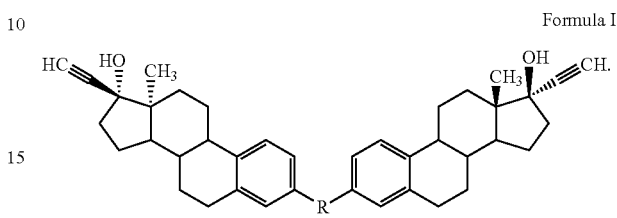

Formula I and pharmaceutically acceptable salts thereof; wherein R is selected from the group consisting of

wherein X and Y are independently selected from

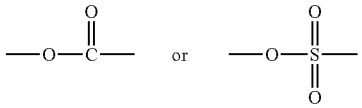

and Z is (i) an aliphatic straight chain having 1 to 10 carbon atoms which may be saturated or unsaturated and optionally may be substituted by one or more lower alkyl, hydroxy or amino groups, (ii)

wherein A and D are independently
—CO(CH$_2$)$_f$—, wherein f is 0 to 5, and B is —O—(CH$_2$CH$_2$O)$_p$—, wherein p is 1 to 700, or (iii) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid.

The present invention also includes a pharmaceutical dosage unit comprising (a) a di-steroidal prodrug of ethinyl estradiol according to formula I, and (b) one or more pharmaceutically acceptable excipients. In a particularly preferred embodiment, a progestogen is included in the pharmaceutical dosage unit.

The present invention also includes a method for forming a di-steroidal prodrug of ethinyl estradiol having the structure of formula I, comprising the step of reacting ethinyl estradiol and a linking agent under conditions effective to form the di-steroidal prodrug of ethinyl estradiol. Optionally, the process may include further purification steps such as chromatography or recrystallization.

In another aspect of the present invention, a method of providing contraception is provided. The method comprises the step of administering to a patient in need thereof, an effective amount of a di-steroidal prodrug of ethinyl estradiol of the invention, preferably in combination with a progestogen, for an effective period of time.

In yet another aspect of the invention, a method of providing hormone treatment therapy is provided. The method comprises the step of administering to a patient in need thereof, an effective amount of a di-steroidal prodrug of ethinyl estradiol of the invention, for an effective period of time.

DETAILED DESCRIPTION OF THE INVENTION

For the purposes of the present invention, a prodrug is an entity which either comprises an inactive form of an active drug or includes a chemical group which confers preferred characteristics on the drug.

For the purposes of the present invention, room temperature is understood to mean 25° C.+/−5° C.

In the present invention, the di-steroidal prodrug of ethinyl estradiols have ethinyl estradiol moieties that are linked by a divalent linking group R at the 3'C position of the ethinyl estradiol moiety. The linking group R in a particularly preferred embodiment may be selected from the group consisting of a carbonate group or a dicarboxylic group having an aliphatic backbone of 2 to 10 carbon atoms which may be saturated or unsaturated, straight or branched, and which optionally may be substituted by amino, hydroxyl, or lower alkyl. As used herein lower alkyl is a straight chain or branched aliphatic group having 1 to 6 carbon atoms. In another embodiment R may be a dicarboxylic group having a polyoxyethylene backbone. In yet a further embodiment the linking group may be a peptide with a carboxylic acid function at each end.

In the present invention, the di-steroidal prodrug of ethinyl estradiol has the structural formula:

Formula I

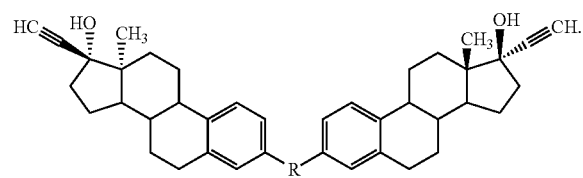

wherein R is selected from the group consisting of

wherein X and Y are independently selected from

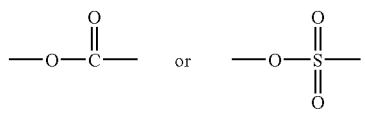

Z is
(i) an aliphatic straight chain having 1 to 10 carbon atoms which may be saturated or unsaturated and optionally may be substituted by one or more lower alkyl, hydroxy or amino groups,
(ii)

wherein A and D are independently
—CO(CH$_2$)$_f$—, wherein f is 0 to 5, and B is —O—(CH$_2$CH$_2$O)$_p$—, wherein p is 1 to 700, or
(iii) peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid.

It should be apparent that when Y and X are a carboxylic or sulfonic group that the carbonyl or sulfur of those groups is bound to Z. Thus, in a preferred embodiment when Y and X are both carbonyl then R is

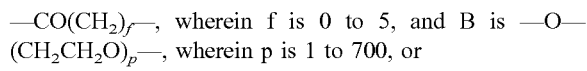

It should be further apparent to one of ordinary skill in the art that the stereochemical conformation of each ethinyl estradiol moiety in the di-steroidal prodrug will be dependent on the structural conformation of R.

In a preferred embodiment, R is selected from the group consisting of:

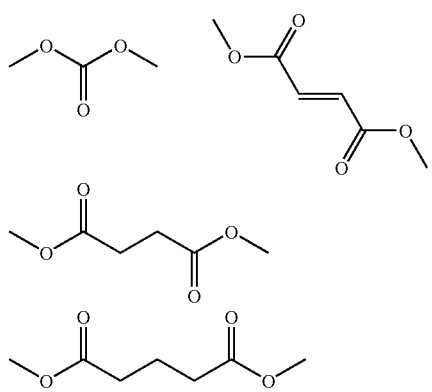

-continued
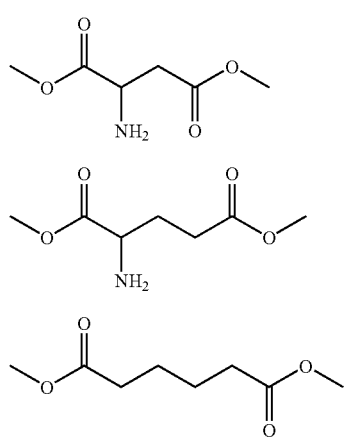
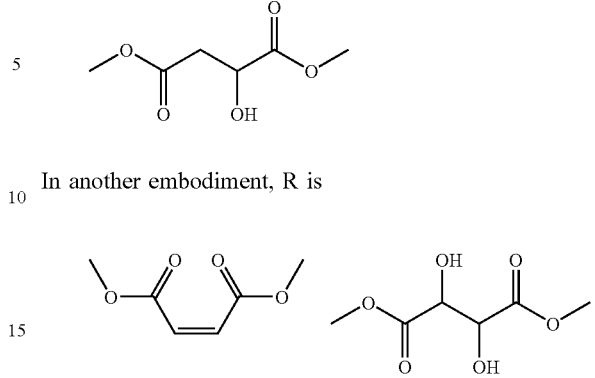
In another embodiment, R is
Preferably, the di-steroidal prodrug of ethinyl estradiol is selected from the group consisting of
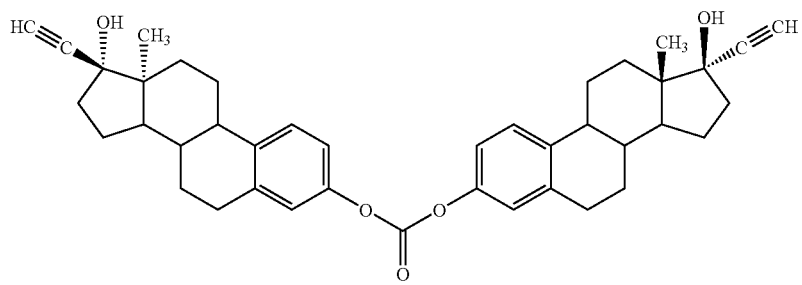
di-(3-ethinyl estradiol) carbonate,
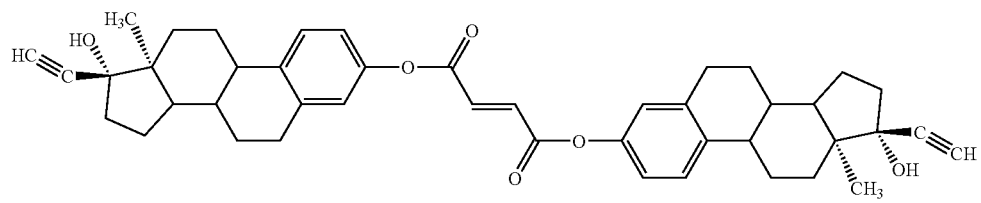
di-(3-ethinyl estradiol) fumarate,
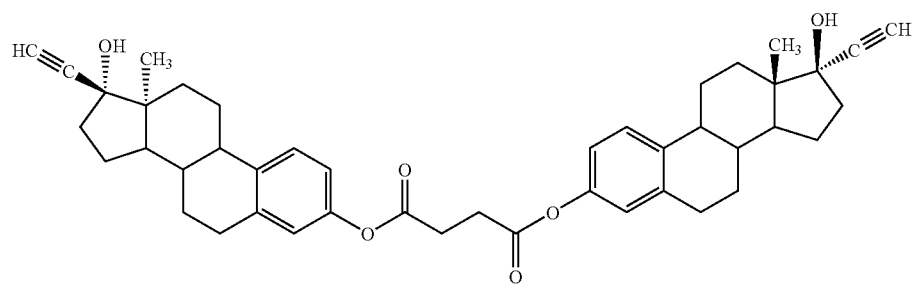
di-(3-ethinyl estradiol) succinate,

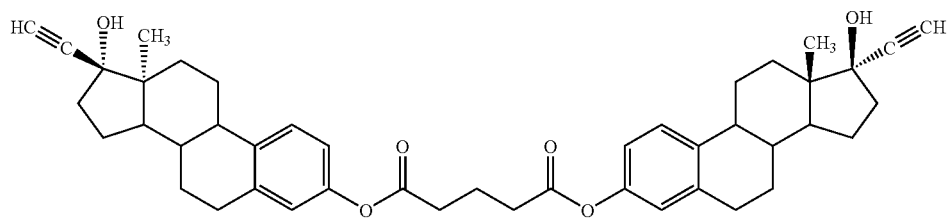
di-(3-ethinyl estradiol) glutarate,
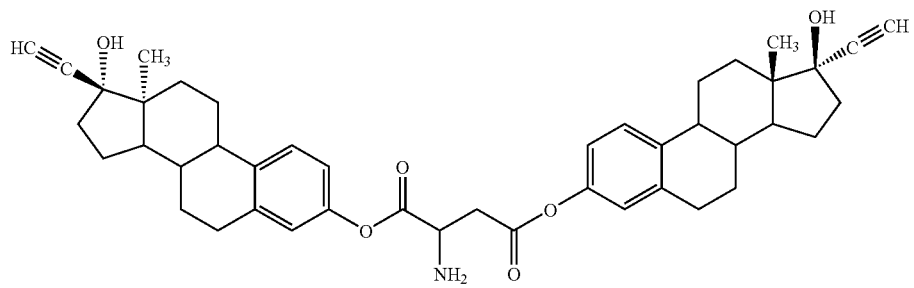
di-(3-ethinyl estradiol) aspartate,
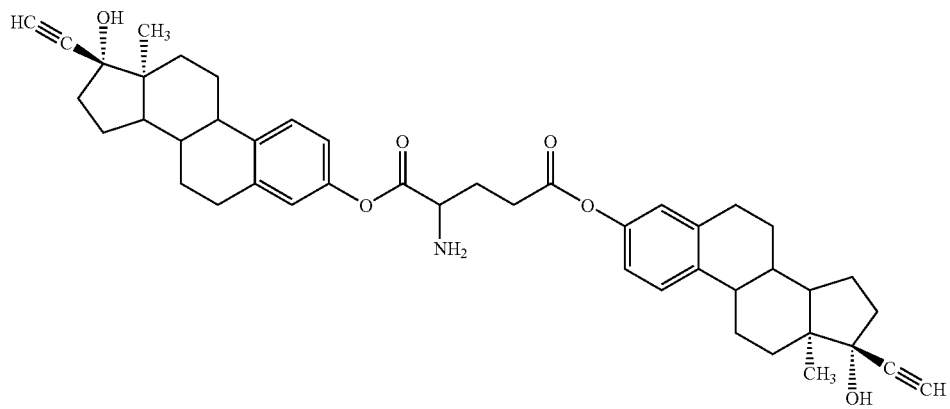
di-(3-ethinyl estradiol) glutamate,
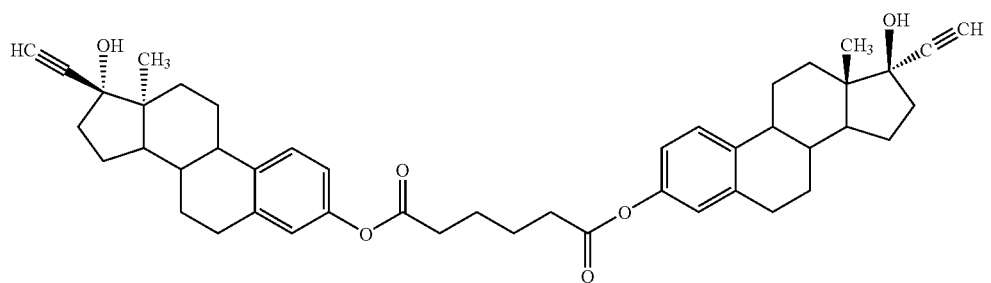

di-(3-ethinyl estradiol) adipate,

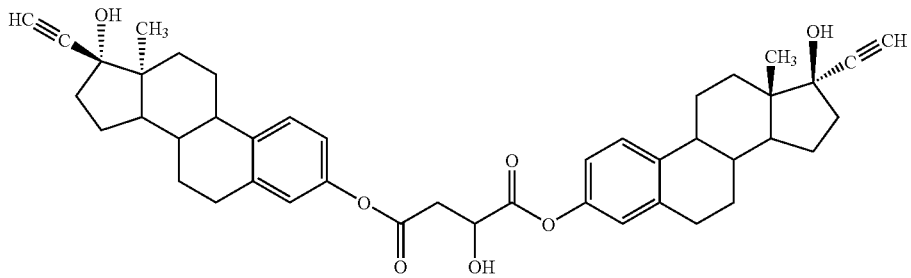

di-(3-ethinyl estradiol) malate, and pharmaceutically acceptable salts thereof.

As used herein, the phrase "pharmaceutically acceptable salt" refers to a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, g-hydroxybutyrates, glycollates, tartrates, methane-sulfonates (mesylates), propanesulfonates, naphthalene-1-sulfonates, naphthalene-2-sulfonates, and mandelates. A desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like. In the present invention the hydrochloride salt is the preferred salt.

A pharmaceutical dosage unit may be formulated to include the di-steroidal prodrug of ethinyl estradiol of the present invention in combination with one or more pharmaceutically acceptable excipients.

Excipients useful herein include a wide variety of additives, or ingredients, such as for example, fillers, diluents (solid and liquid), biocompatable polymers (such as organopolysiloxanes, polyurethanes and polymethylacrylates), skin penetrators and penetration enhancers, solubilizers, lubricants, stabilizers, flow control agents, colorants, glidants, effervescent agents, sweeteners, flavors, perfumes, and the like.

Other steroids, e.g., progestogens may be included in the pharmaceutical dosage unit. Exemplary progestogens include norethindrone, norethindrone acetate, norgestrel, levonorgestrel, desogestrel, 3-ketodesogestrel, gestodene, medroxyprogesterone acetate and the like.

The pharmaceutical dosage unit may be in an orally ingestible form, such as tablets, capsules, chewable tablets or capsules, troche, liquid suspensions, pills, or sustained release dosage forms. Alternatively, the pharmaceutical dosage unit may be a transdermal delivery system. Or in another embodiment the pharmaceutical dosage unit may be a topical composition such as a gel, cream, ointment, liquid and the like. Or in another alternative embodiment, the pharmaceutical dosage unit may be designed for vaginal administration e.g., a vaginal ring.

The steroidal prodrugs of ethinyl estradiol may be synthesized using the methods described herein. These methods may be modified or alternative synthesis methods may be employed as desired. The synthesis methods typically begin with ethinyl estradiol as the starting material, but could also begin with estrone. It should be understood, however, that where ethinyl estradiol is indicated, derivatives of ethinyl estradiol may be used.

In general, the di-steroidal prodrug of ethinyl estradiol of the invention is formed by reacting ethinyl estradiol or a derivative thereof and a suitable linking agent under conditions effective to form the di-steroidal prodrug of ethinyl estradiol.

One method for synthesizing a di-steroidal ester of ethinyl estradiol of this invention is by reacting ethinyl estradiol or a derivative thereof with a carbonate linking agent and a coupling agent in the presence of a base. The resulting compound is di-(3-ethinyl estradiol) carbonate. The reaction is depicted in Reaction Sequence 1.

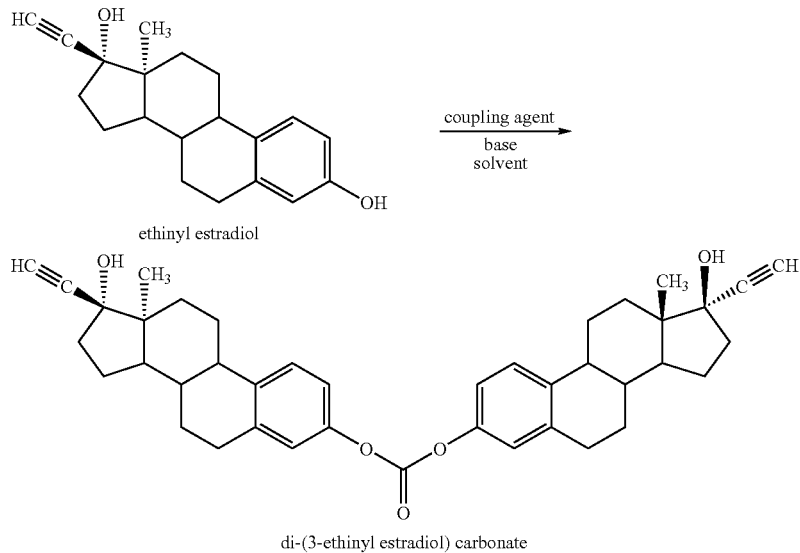

In a preferred embodiment, bis(4-nitrophenyl) carbonate (b-NPC) serves as the carbonate linking agent and coupling agent, 4-dimethylamino pyridine (DMAP) is selected as the base, and tetrahydrofuran (THF) is selected as the solvent.

Another method that may be used to synthesize a di-steroidal prodrug of ethinyl estradiol of this invention comprises reacting ethinyl estradiol or a derivative thereof with an aliphatic diacid that has 1 to 10 carbon atoms, i.e., n is an integer from 1 to 10, which may be saturated or unsaturated and optionally may be substituted by one or more lower alkyl, hydroxy or amino groups. The aliphatic diacid is the linking agent and may be, for example, succinic acid, tartaric acid, malic acid, glutaric acid, adipic acid, fumaric acid, maleic acid, glutamic acid or aspartic acid. In one embodiment, a coupling agent can be reacted with a diacid in the presence of a base catalyst as shown in Reaction Sequence 2.

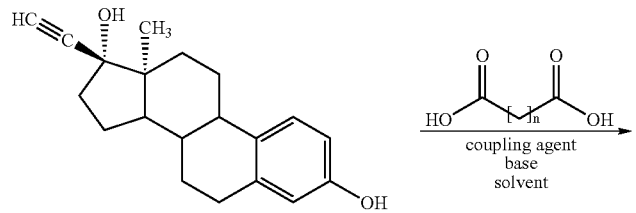

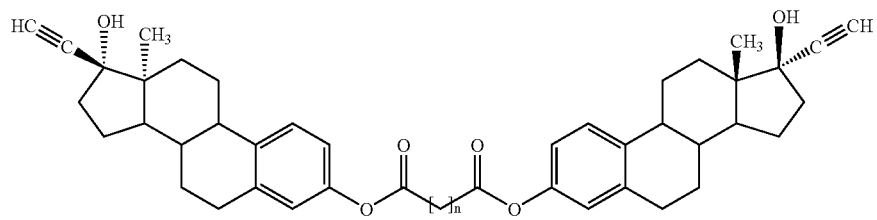

Reaction Sequence 2A shows a preferred embodiment where the coupling agent is 1-(3-dimethylaminopropyl)-3-ethyl-carbodiimide hydrochloride (EDCI) and the base catalysts are 4-dimethylamino pyridine (DMAP) and triethylamine. The solvent used to carry out the reaction is preferably chloroform, although as one skilled in the art will readily recognize, many other organic solvents may be suitable.

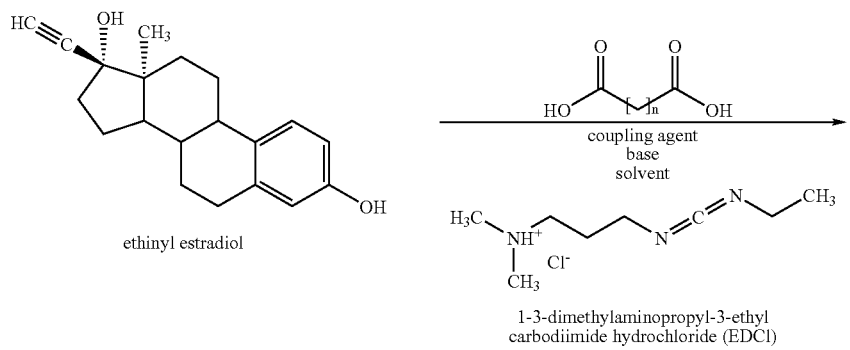

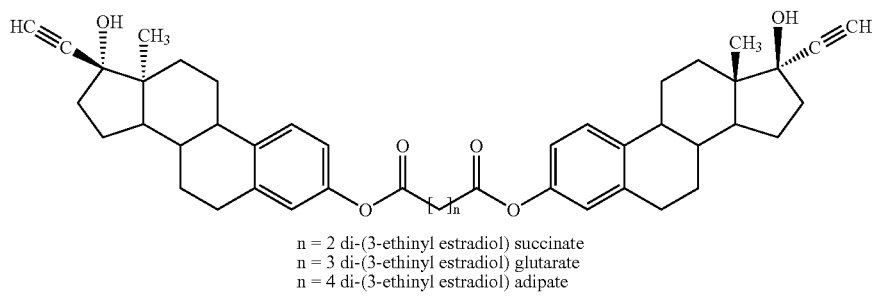

The prodrug compound of this invention may also be synthesized by reacting ethinyl estradiol or a derivative thereof directly with a linking agent having the formula

G—CO—Z—X—G wherein G is a halogen and Z and X are defined as previously noted. The preferred halogens are chloro and bromo. For example, the linking agent may be a di-acyl chloride, which reacts with ethinyl estradiol in the presence of a base, as depicted in Reaction Sequence 3.

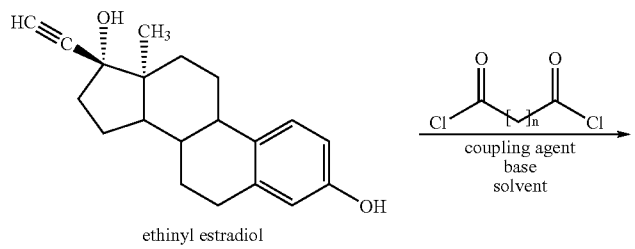

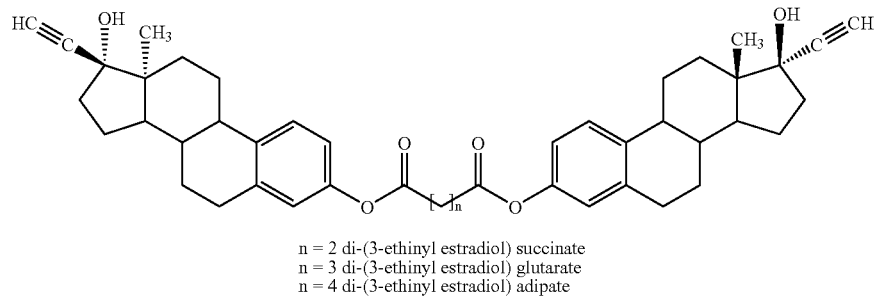

n = 2 di-(3-ethinyl estradiol) succinate
n = 3 di-(3-ethinyl estradiol) glutarate
n = 4 di-(3-ethinyl estradiol) adipate

15 n is an integer from 1 to 10.

Utilizing Reaction Sequence 3, DMAP and triethylamine may be employed as the base catalysts.

Yet another method for forming the di-steroidal prodrug of ethinyl estradiol of the invention is with a diacid amino acid, such as aspartic acid or glutamic acid, as the linking agent.

Reaction Sequence 4 exemplifies such a synthesis mechanism.

Reaction Sequence 4

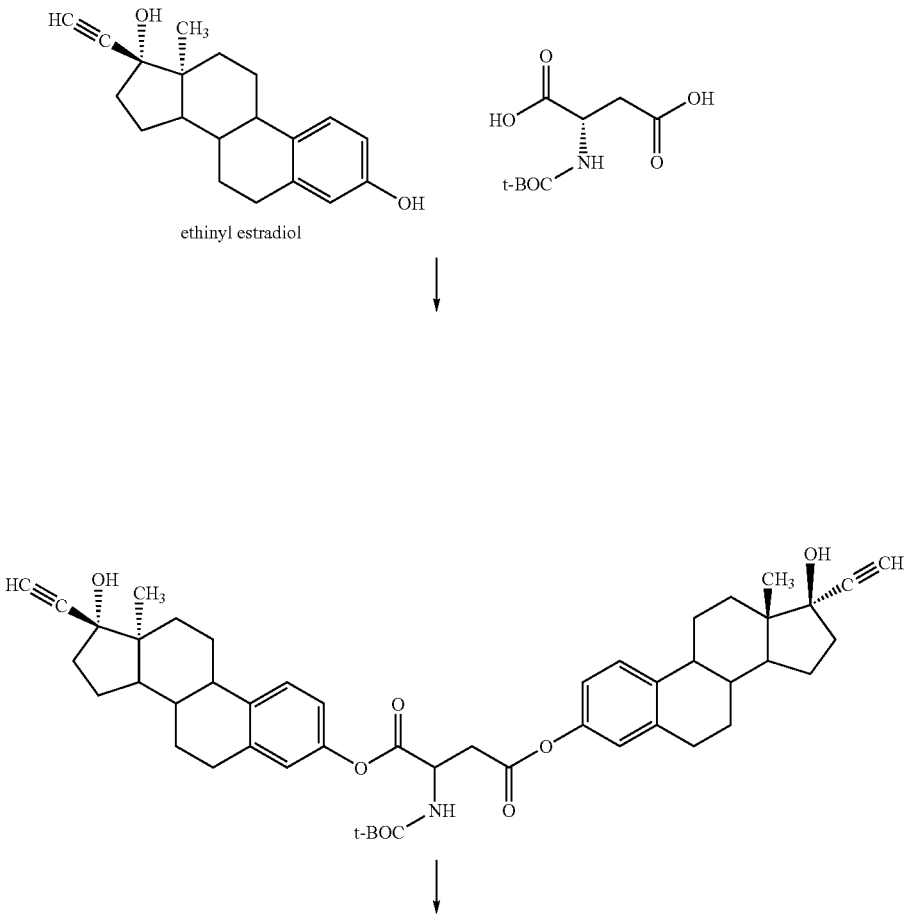

-continued
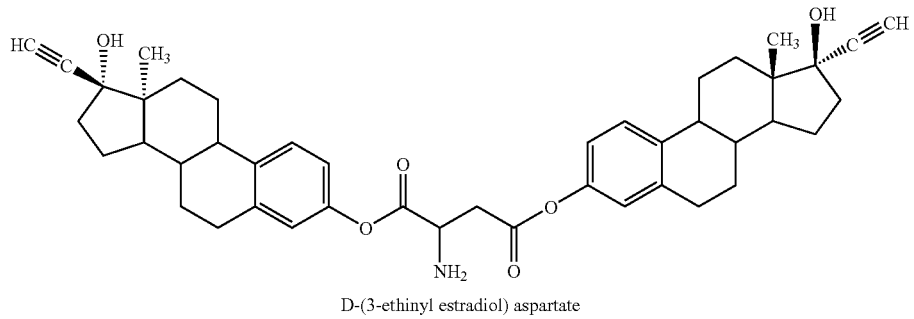
D-(3-ethinyl estradiol) aspartate
Di-steroidal prodrug of ethinyl estradiols may also be synthesized where tert-butoxycarbonyl cysteic acid serves as the linking agent, as depicted in Reaction Sequence 5.
Reaction Sequence 5
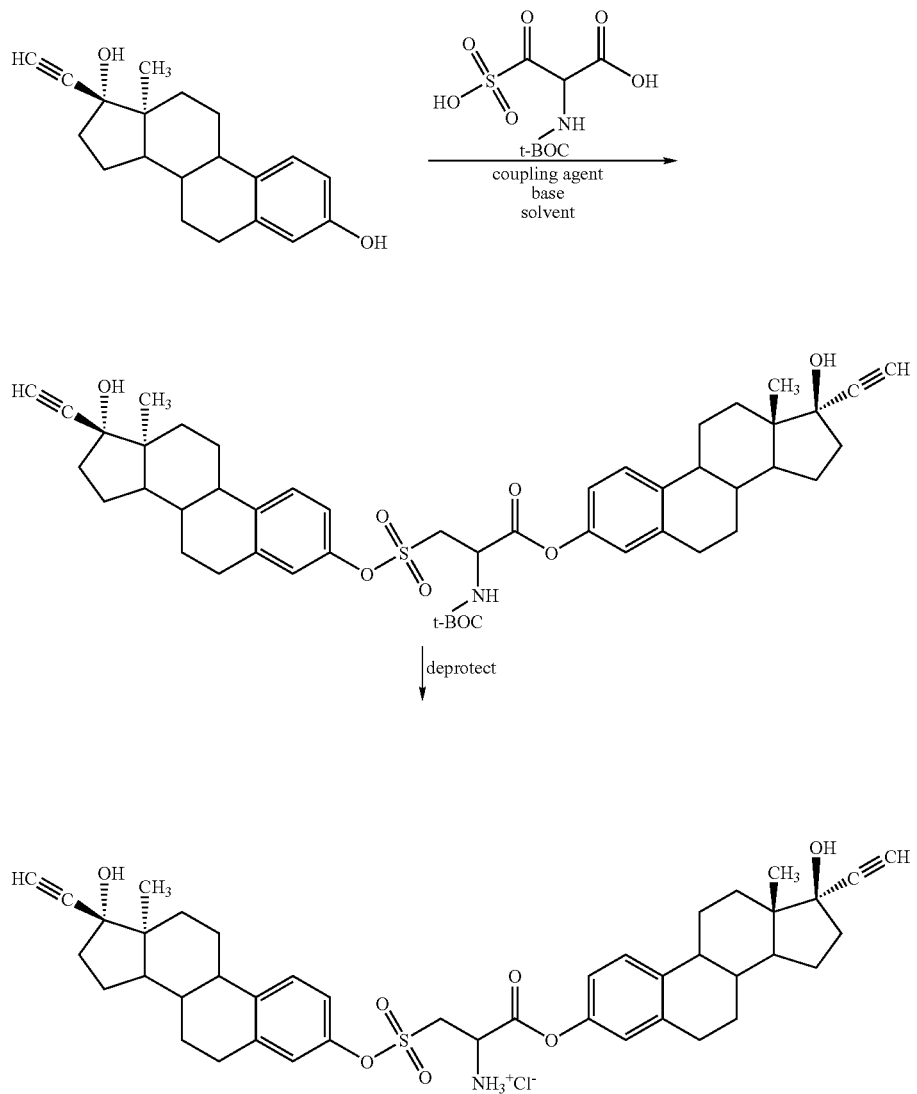

Alternatively, polyethylene glycol can be reacted with succinic anhydride to produce a diacid linking agent that connects the ethinyl estradiol moieties at the 3'C position, as depicted in Reaction Sequence 6.

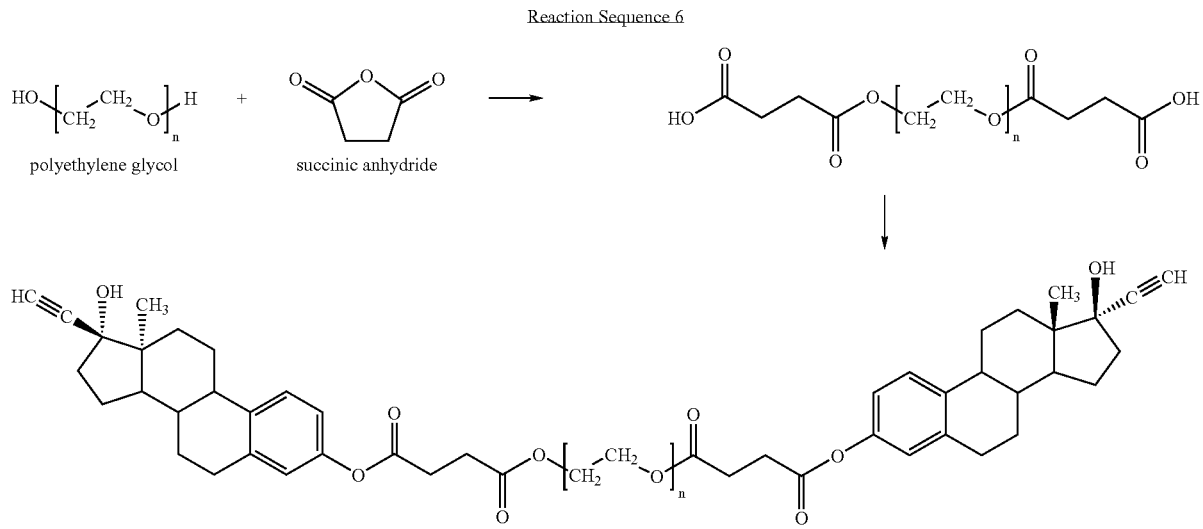

Reaction Sequence 6 wherein n is an integer from 1 to 700. Preferably n is 4 to 200, and more preferably n is 4 to 60.

Moreover, ethinyl estradiol may be reacted with a dipeptide or any suitable length of peptide, which serves as the linking agent. The peptide linking agent will have 2 to 15 units derived from amino acids, such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and combinations thereof. The end groups of the peptide are derived independently from aspartic acid or glutamic acid to form the divalent linking agent. From 2 to 15 amino acids may be linked together to form the peptide linker so long as the amino acids attached at the ends are aspartic acid, glutamic acid or a combination thereof. Preferably, 2 to 12 amino acids are linked together to form the peptide. More preferably, 2 to 5 amino acids form the divalent peptide. For example, the dipeptide Gly-Asp-Boc with the amine function protected with n-(tert butoxycarbonyl) can act as the linking group, as shown in Reaction Sequence 7.

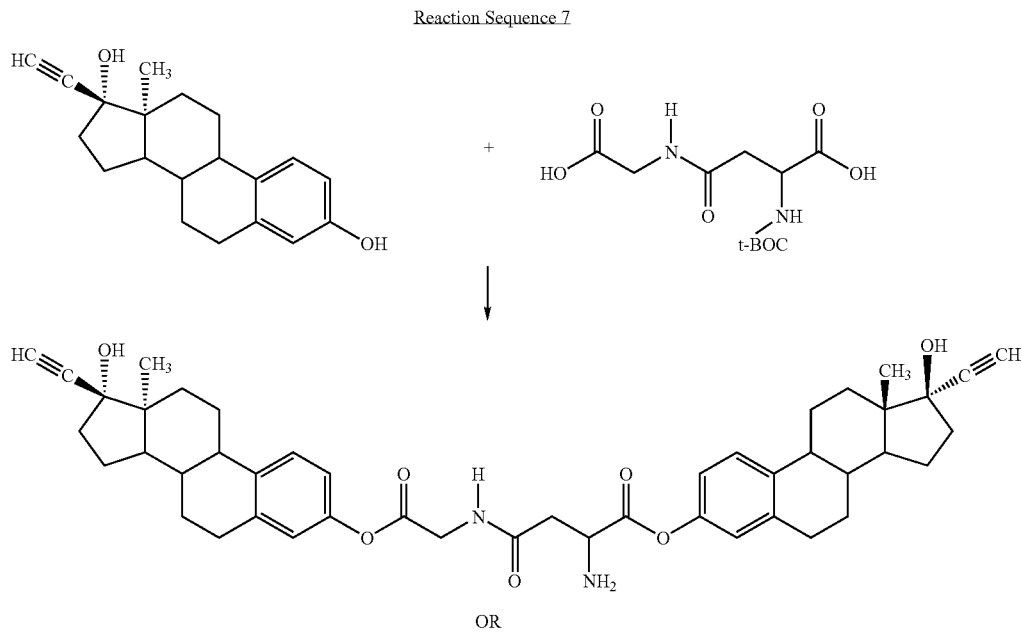

Reaction Sequence 7

OR

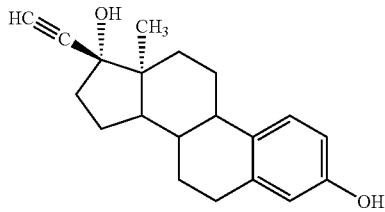
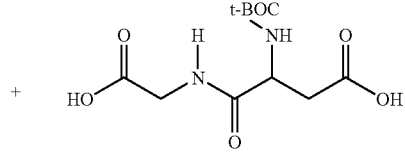

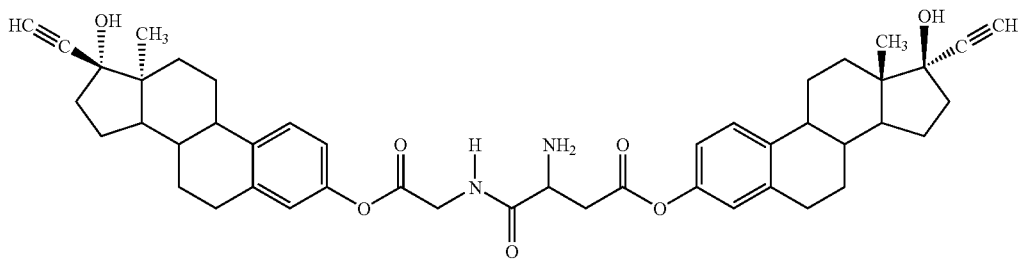

Preferably, the linking agents that are used to form the di-steroidal prodrug of ethinyl estradiol of the invention are carbonate, H—Y—Z—X—H, or

G—CO—Z—X—G wherein G is a halogen. Z may be a divalent peptide group.

Coupling agents that may be used in synthesizing the di-steroidal prodrug of ethinyl estradiol of the present invention, may be for example, b-NPC, EDCI, and mixtures thereof. Alternative compounds may be used, so long as they fulfill the intended purpose.

In the synthesis reactions described, a base may be used as a catalyst. Suitable bases include, but are not limited to DMAP, triethylamine, or mixtures thereof.

Solvents that may be used in the synthesis reactions are for example, tetrahydrofuran (THF), chloroform, dichloromethane, and the like.

To increase the purity of the di-steroidal prodrug of ethinyl estradiol, the prodrug may be treated to one or more washing steps, and/or recrystallization steps.

The washing step may be used to rinse the precipitate that is formed by the di-steroidal prodrug of ethinyl estradiol. As noted, one or more washing steps may be used. Water, sodium hydroxide, or any suitable alternative can be generally used for washing purposes.

As previously noted, the purity may be increased by subjecting the di-steroidal prodrug to one or more recrystallization steps. The recrystallization step may be performed by various methods, and using suitable solvents such as but not limited to ethyl acetate, heptane or THF, or mixtures thereof.

The drying step in the synthesis may be conducted by various methods including but not limited to, air drying, vacuum drying, oven drying, filtration, and the like. Drying may be enhanced by using a drying agent such as magnesium sulphate to assist in drying the product.

The di-steroidal prodrug of ethinyl estradiol compounds of the present invention have been characterized using various analytical methods. For example, high performance liquid chromatography (HPLC) was used to establish the purity of the synthesized product. $^1$H and $^{13}$C nuclear magnetic resonance (NMR), mass spectrometry and infrared (IR) spectroscopy were used to verify its structure. Moreover, the product was further characterized by determining the melting point.

The di-steroidal prodrug of ethinyl estradiol of the present invention may be used for providing contraception. A therapeutically effective amount of the di-steroidal prodrug of ethinyl estradiol of the invention is administered to a patient in need thereof, for an effective period of time. Preferably, the di-steroidal prodrug is administered in combination with a progestogen.

The di-steroidal prodrug of ethinyl estradiol of the invention can also be used in providing hormone treatment therapy. Such a method of treatment would comprise the step of administering to a patient in need thereof, a therapeutically effective amount of a di-steroidal prodrug of ethinyl estradiol of the invention, for an effective period of time.

The prodrugs of ethinyl estradiol of the present invention are administered in a "therapeutically effective amount." This is understood to mean a sufficient amount of a compound or dosage unit that will positively modify the symptoms and/or condition to be treated. The therapeutically effective amount can be readily determined by those of ordinary skill in the art, but of course will depend upon several factors. For example, one should consider the condition and severity of the condition being treated, the age, body weight, general health, sex, diet, and physical condition of the patient being treated, the duration of the treatment, the nature of concurrent therapy, the particular active ingredient being employed, the particular pharmaceutically-acceptable excipients utilized, the time of administration, method of administration, rate of excretion, drug combination, and any other relevant factors. Typically, the amount of prodrug of ethinyl estradiol of this invention administered on a daily basis will have a potency equivalent to about 0.025 to about 100 mcg of ethinyl estradiol.

The prodrugs of the invention are preferably administered orally or vaginally. The prefered dosage forms are tablets or vaginal rings.

Specific embodiments of the invention will now be demonstrated by reference to the following examples. It should be understood that these examples are disclosed solely by way of illustrating the invention and should not be taken in any way to limit the scope of the present invention.

EXAMPLE 1

Synthesis of Di-(3-Ethinyl Estradiol) Carbonate

Preparation

Ethinyl estradiol (20.0 g, 0.068 mol), b-NPC (10.3 g, 0.034 mol), 4-DMAP (0.85 g, 0.007 mol) and THF (200 mL) were added to a 500 mL 3-necked round-bottomed flask fitted with a magnetic stirrer. The reaction mixture was stirred at room temperature for about 18 hours. The reaction mixture was poured into 500 mL of water and a yellow precipitate formed. 2M hydrochloric acid (25 mL) was used to extract the mixture with stirring. The yellow precipitate turned white.

The resulting reaction mixture was filtered and the precipitate was washed thoroughly with 500 mL of water and filtered. The precipitate was then thoroughly washed with 500 mL of 1M sodium hydroxide and filtered.

The precipitate was then thoroughly washed with 500 mL of water and filtered. The resulting di-(3-ethinyl estradiol) carbonate was dried in a vacuum oven overnight (about 18 hrs) at 40° C.

Recrystallization Method

Di-(3-ethinyl estradiol) carbonate (18.1 g) and ethyl acetate (1 L) were added into a 3-necked round-bottomed flask fitted with a condenser and magnetic stirrer. The mixture was heated to reflux. The hot mixture was filtered. The filtrate was allowed to cool and recrystallized slowly. Next, the di-(3-ethinyl estradiol) carbonate was allowed to air dry.

The compound was analyzed by HPLC and found to be 98.5% pure. Structural analysis by $^{13}$C and $^{1}$H NMR and IR spectroscopy revealed that the 3'C to 3'C carbonate prodrug had formed. Mass Spectroscopy revealed formation of the compound. The melting point was found to be 235° C.

EXAMPLE 2

Synthesis of Di-(3-ethinyl estradiol) Succinate

Preparation

Succinic acid (3.17 g; 0.027 mol) was placed into a 500 mL 3-necked round-bottomed flask fitted with a magnetic stirrer. Chloroform (300 mL) was added and the mixture was stirred. EDCI (1.2 g, 0.094 mol) and triethylamine (12 mL) were added and stirred for about 15 minutes. Ethinyl estradiol (15 g; 0.051 mol) was then added, followed by 4-dimethylamino pyridine (0.93 g, 0.007 mol). The resulting solution was stirred for about 18 hours at room temperature and then the reaction mixture was diluted with chloroform (500 mL). A 2M hydrochloric solution (2×400 mL) and then brine (400 mL) was used to extract the solution. Finally saturated sodium bicarbonate solution (2×400 mL) was used to extract the solution. The resulting di-(3-ethinyl estradiol) succinate was dried over magnesium sulfate, filtered, and concentrated.

Recrytallization Method

The di-(3-ethinyl estradiol) succinate (10 g) and a mixture of ethyl acetate/heptane (50:50; 200 mL) were placed into a 3-necked round-bottomed flask fitted with a condenser and magnetic stirrer. The mixture was heated to reflux so that nearly all the ethinyl estradiol ester dissolved. The hot mixture was then filtered. The filtrate was allowed to cool and recrystallized slowly (about 18 hrs). Next, the di-(3-ethinyl estradiol) succinate was filtered and allowed to air dry. This was followed by drying in a vacuum oven at room temperature for about 18 hours.

The compound was analyzed by HPLC and found to be 97.8% pure. Structural analysis by $^{13}$C and $^{1}$H NMR and IR spectroscopy revealed that the 3'C to 3'C linked prodrug had formed. The melting point was found to be 198° C.

EXAMPLE 3

Synthesis of Di-(3-Ethinyl Estradiol) Glutarate

Preparation

Glutaric acid (3.43 g; 0.027 mol) was placed into a 500 mL 3-necked round-bottomed flask fitted with a magnetic stirrer. Chloroform (300 mL) was added and the mixture was stirred. EDCI (14.1 g, 0.073 mol) and triethylamine (12 mL) were added and stirred for about 15 minutes. Ethinyl estradiol (15 g; 0.051 mol) was then added, followed by 4-DMAP (1.5 g, 0.012 mol). The solution was stirred for about 18 hours at room temperature. The reaction mixture was then diluted with chloroform (250 mL) and extracted with a 1M hydrochloric acid solution (2×500 mL) and then a brine (400 mL) solution. Finally saturated sodium bicarbonate solution (500 mL then 250 mL) was used to extract the solution. The organic layer was dried over magnesium sulfate, filtered and concentrated to give di-(3-ethinyl estradiol) glutarate.

Recrystallization Method

The di-(3-ethinyl estradiol) glutarate (10.6 g) and a mixture of ethyl acetate/heptane (50:50; 200 mL) were placed into a 3-necked round-bottomed flask fitted with a condenser and magnetic stirrer. The mixture was heated to reflux so that nearly all the ethinyl estradiol ester dissolved. The hot mixture was filtered. The filtrate was allowed to cool and recrystallized slowly (about 18 hrs). Di-(3-ethinyl estradiol) glutarate was filtered and allowed to air dry. This was followed by drying in a vacuum oven at room temperature for about 18 hours.

The compound was analyzed by HPLC and found to be 96.0% pure. Structural analysis by $^{13}$C and $^{1}$H NMR and IR spectroscopy revealed that the 3'C to 3'C prodrug had formed. The melting point was found to be 194° C.

EXAMPLE 4

Synthesis of Di-(3-Ethinyl Estradiol) Adipate

Preparation

Adipic acid (3.8 g; 0.026 mol) was placed into a 500 mL 3-necked round-bottomed flask fitted with a magnetic stirrer. Chloroform (300 mL) was added and the mixture was stirred. EDCI (14.1 g, 0.073 mol) and triethylamine (12 mL) were added and stirred for about 15 minutes. Ethinyl estradiol (15 g; 0.051 mol) was then added, followed by 4-dimethylamino pyridine (1.5 g, 0.012 mol). The resulting solu tion was stirred for about 18 hours at room temperature. The reaction mixture was diluted with chloroform (500 mL) and extracted with a 2M hydrochloric acid solution (2×400 mL) and then brine (400 mL). Finally saturated sodium bicarbonate solution (2×400 mL) was used to extract the solution. The organic layer was dried over magnesium sulfate, filtered and concentrated to give di-(3-ethinyl estradiol) adipate.

Recrystallization Method

The di-(3-ethinyl estradiol) adipate (9 g) and a mixture of ethyl acetate/heptane (50:50; 150 mL) were placed into a 3-necked round-bottomed flask fitted with a condenser and magnetic stirrer. The mixture was heated to reflux so that nearly all the ethinyl estradiol ester dissolved. The hot mixture was then filtered. The filtrate was allowed to cool and recrystallized slowly (about 18 hrs). Di-(3-ethinyl estradiol) adipate was filtered and allowed to air dry. This was followed by drying in a vacuum oven at room temperature for about 18 hours.

The compound was analyzed by HPLC and found to be 90.9% pure. Structural analysis by $^{13}$C and $^1$H NMR and IR spectroscopy revealed that the 3'C to 3'C prodrug had formed. The melting point was found to be 179° C.

EXAMPLE 5

Synthesis of Di-(3-Ethinyl Estradiol) Fumarate

Preparation

Ethinyl estradiol (25 g; 0.085 mol) was placed into a 1 L 3-necked round-bottomed flask fitted with a magnetic stirrer. Dichloromethane (375 mL) was added and the mixture was stirred at room temperature under nitrogen. Triethylamine (15 mL) was added. The flask was placed in an ice/water bath and cooled to 0° C. 4-DMAP (0.78 g, 0.006 mol) was then added. The solution was stirred for about 15 minutes at 0° C. Fumaryl chloride (7.14 g; 0.047 mol) was dissolved in dichloromethane (125 mL). The fumaryl chloride solution was added dropwise via an addition funnel to the ethinyl estradiol solution, while maintaining the temperature below 5° C. After final addition, the solution was slowly warmed to room temperature and then stirred (about 20 hours) at room temperature under nitrogen. The suspension that resulted was diluted with dichloromethane (1 L) and filtered to capture any solids. The solids were then washed with dichloromethane (500 mL) and a 2M hydrochloric acid solution (500 mL). The organic phase was separated and extracted with 2M hydrochloric acid (500 mL), sodium hydrogen carbonate solution (2×500 mL) and brine (500 mL). The resulting di-(3-ethinyl estradiol) fumarate was dried over magnesium sulphate, filtered, and concentrated. The solids were dissolved in fresh dichloromethane (1000 mL). Decolorizing charcoal (35 g) was added to the mixture, which was then heated to 40° C. for about 30 minutes. The solids were then filtered on a bed of celite and rinsed with dichloromethane (500 mL). The yellow filtrate was then concentrated.

Recrystallization Method

The di-(3-ethinyl estradiol) fumarate (14.6 g) and a mixture of THF/heptane (2:1; 300 mL) were placed into a 3-necked round-bottomed flask fitted with a condenser and magnetic stirrer. The mixture was heated to reflux. The hot mixture was then filtered to remove the insoluables. The filtrate was allowed to cool and recrystallized slowly (about 18 hrs). The resulting di-(3-ethinyl estradiol) fumarate was filtered and allowed to air dry. This was followed by drying in a vacuum oven at room temperature for about 18 hours.

The compound was analyzed by HPLC and found to be 98.4% pure. Structural analysis by $^{13}$C and $^1$H NMR and IR spectroscopy revealed that the 3'C to 3'C prodrug had formed. The melting point was found to be 260° C.

EXAMPLE 6

Synthesis of Di-(3-Ethinyl Estradiol) Aspartate (Boc Protected)

Preparation-Step 1

N-(tert-butoxycarbonyl)aspartic acid (8.65 g; 0.037 mol) was placed into a 1 L 3-necked round-bottomed flask fitted with a magnetic stirrer. Chloroform (400 mL) was added and the mixture was stirred. EDCI (24 g, 0.125 mol) and triethylamine (16 mL) were added and stirred for about 15 minutes. Ethinyl estradiol (20 g; 0.067 mol) was then added, followed by 4-DMAP (2.0 g, 0.016 mol). The solution was stirred for about 20 hours at room temperature under a nitrogen atmosphere. The reaction mixture was diluted with chloroform (500 mL), washed with a 2M hydrochloric acid solution (2×500 mL), then brine (500 mL), and finally saturated sodium bicarbonate solution (2×500 mL). The organic phase was dried over magnesium sulphate, filtered, and concentrated to afford di-(3-ethinyl estradiol) aspartate, as a white solid, which gave a purity by HPLC of 80.0%. This crude material was purified by HPLC.

The compound was analyzed by HPLC and found to be 94.0% pure. Structural analysis by $^{13}$C and $^1$H NMR and IR spectroscopy revealed that the 3'C to 3'C prodrug had formed. The melting point was found to be 141° C.

Preparation Step 2—Deprotecting Reaction to Produce Di-(3-Ethinyl Estradiol) Aspartate.

The boc protected Aspartate ethinyl estradiol ester (26 g; 0.033 mol) was placed into a 500 mL 3-necked round-bottomed flask fitted with a magnetic stirrer. 4M hydrochloric acid in dioxane (130 mL) was added and the mixture was stirred for about 18 hours at room temperature under nitrogen. Excess hydrochloric acid and dioxane were removed under reduced pressure. DCM (300 mL) was added. The solid was dissolved completely and the solvent was removed under reduced pressure.

The residue was slurried in ethyl acetate, filtered and washed in heptane and dried to afford a white solid.

The compound was analyzed by HPLC and found to be 97.0% pure. Structural analysis by $^{13}$C and $^1$H NMR and IR spectroscopy revealed that the 3'C to 3'C prodrug had formed. The melting point was found to be 183–184° C.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A di-steroidal prodrug of ethinyl estradiol having the following formula:

[Structure of di-steroidal ethinyl estradiol with R linker]

wherein R is selected from the group consisting of

—O—C(=O)—O—   or   Y—Z—X wherein X and Y are independently selected from

—O—C(=O)—   or   —O—S(=O)(=O)— and Z is
  (i) an aliphatic straight chain having 1 to 10 carbon atoms which may be saturated or unsaturated and optionally may be substituted by one or more lower alkyl, hydroxy or amino groups,
  (ii)

A—B—D wherein A and D are independently
—CO(CH$_2$)$_f$—, wherein f is 0 to 5, and B is —O—(CH$_2$CH$_2$O)$_p$—, wherein p is 1 to 700, or
  (iii) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid.

2. The prodrug of claim 1, wherein R is

—O—C(=O)—O—   or   —O—C(=O)—Z—C(=O)—O—.

3. The prodrug of claim 1, wherein R is selected from the group consisting of:

[dimethyl carbonate structure],

[dimethyl fumarate structure],

[dimethyl succinate structure],

[dimethyl glutarate structure],

[dimethyl 2-aminoglutarate structure],

[dimethyl aspartate structure],

[dimethyl adipate structure], and

[dimethyl malate structure].

4. The prodrug of claim 1, wherein R is

[dimethyl maleate/hydroxy structure]   or

[dimethyl tartrate structure].

5. The prodrug of claim 1, wherein said prodrug is selected from the group consisting of di-(3-ethinyl estradiol) carbonate, di-(3-ethinyl estradiol) malate, di-(3-ethinyl estradiol) succinate, di-(3-ethinyl estradiol) glutarate, di-(3-ethinyl estradiol) adipate, di-(3-ethinyl estradiol) fumarate, di-(3-ethinyl estradiol) glutamate, di-(3-ethinyl estradiol) aspartate, and pharmaceutically acceptable salts thereof.

6. A pharmaceutical dosage unit comprising:
  (a) a di-steroidal prodrug of ethinyl estradiol having the following formula:

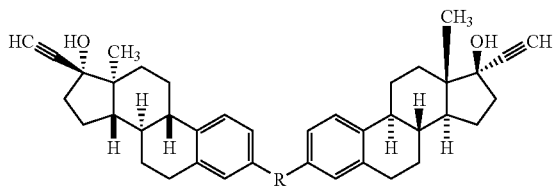

wherein R is selected from the group consisting of

wherein X and Y are independently selected from

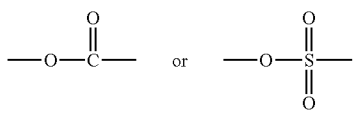

and Z is
- (i) an aliphatic straight chain having 1 to 10 carbon atoms which may be saturated or unsaturated and optionally may be substituted by one or more lower alkyl, hydroxy or amino groups,
- (ii)

A—B—D wherein A and D are independently
—CO(CH$_2$)$_f$—, wherein f is 0 to 5, and B is —O—(CH$_2$CH$_2$O)$_p$—, wherein p is 1 to 700, or
- (iii) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid; and
- (b) one or more pharmaceutically acceptable excipients.

7. A method of synthesizing a di-steroidal prodrug of ethinyl estradiol having the formula

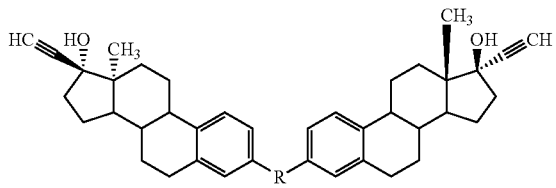

wherein R is selected from the group consisting of

wherein X and Y are independently selected from

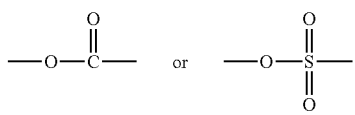

and Z is
- (i) an aliphatic straight chain having 1 to 10 carbon atoms which may be saturated or unsaturated and optionally may be substituted by one or more lower alkyl, hydroxy or amino groups,
- (ii)

A—B—D wherein A and D are independently
—CO(CH$_2$)$_f$—, wherein f is 0 to 5, and B is —O—(CH$_2$CH$_2$O)$_p$—, wherein p is 1 to 700, or
- (iii) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid, comprising the steps of:
- (A) providing ethinyl estradiol or a derivative thereof;
- (B) admixing said ethinyl estradiol and a linking agent, wherein said linking agent is selected from the group consisting of:
  - (a) a carbonate;
  - (b) an aliphatic diacid having a backbone of 1 to 10 carbon atoms;
  - (c) G—CO—Z—X—G wherein G is a halogen;
  - (d) a peptide linkage having 2 to 15 amino acid units derived independently from amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or combinations thereof wherein the end groups of the peptide are amino acid units independently derived from aspartic acid and glutamic acid;
  - (e) a tert-butoxycarbonyl protected cysteic acid; and
  - (f) a polyethylene glycol and succinic anhydride,
- (C) optionally, admixing a coupling agent and/or a base, thereby forming said di-steroidal prodrug of ethinyl estradiol or pharmaceutically acceptable salt thereof.

8. The method of claim 7, wherein said linking agent is a carbonate,

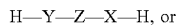

wherein G is a halogen.

9. The method of claim 7, wherein said coupling agent is selected from the group consisting of: bis(4-nitrophenyl) carbonate, 1-(3-dimethylaminopropyl)-3-ethyl-carbodiimide hydrochloride, and mixtures thereof.

10. The method of claim 7, wherein said at least one base is selected from the group consisting of: 4-dimethylamino pyridine, triethylamine, and mixtures thereof.

11. The method of claim 7, wherein said prodrug is di-(3-ethinyl estradiol) carbonate or a pharmaceutically acceptable salt thereof.

12. The method of claim 7, wherein said prodrug is selected from the group consisting of: di-(3-ethinyl estradiol) succinate, di-(3-ethinyl estradiol) malate, di-(3-ethinyl estradiol) glutarate, di-(3-ethinyl estradiol) adipate, di-(3-ethinyl estradiol) fumarate, di-(3-ethinyl estradiol) glutamate, di-(3-ethinyl estradiol) aspartate, and a pharmaceutically acceptable salt thereof.

13. A method of providing contraception comprising the step of:

administering to a patient in need thereof, an effective amount of said di-steroidal prodrug of ethinyl estradiol of claim 1, for an effective period of time.

14. A method of providing hormone treatment therapy to a patient in need thereof, comprising the step of:

administering to said patient in need thereof, an effective amount of said di-steroidal prodrug of ethinyl estradiol of claim 1, for an effective period of time.

* * * * *